(12) United States Patent
Jung et al.

(10) Patent No.: US 11,998,734 B2
(45) Date of Patent: *Jun. 4, 2024

(54) RING ELECTRODE WITH INTERMEDIATE DIFFUSION LAYER

(71) Applicant: Heraeus Deutschland Gmbh & Co. KG, Hanau (DE)

(72) Inventors: Markus Jung, Hanau (DE); Bernd Spaniol, Hanau (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 435 days.

This patent is subject to a terminal disclaimer.

(21) Appl. No.: 17/374,347

(22) Filed: Jul. 13, 2021

(65) Prior Publication Data
US 2022/0008718 A1 Jan. 13, 2022

(30) Foreign Application Priority Data
Jul. 13, 2020 (DE) ...................... 10 2020 118 372.0

(51) Int. Cl.
*A61N 1/05* (2006.01)
*B21C 37/06* (2006.01)
*H01R 13/02* (2006.01)

(52) U.S. Cl.
CPC ............... *A61N 1/056* (2013.01); *B21C 37/06* (2013.01); *H01R 13/025* (2013.01); *H01R 2201/12* (2013.01)

(58) Field of Classification Search
CPC .......... A61N 1/056; A61B 5/263; A61B 5/325
See application file for complete search history.

(56) References Cited

U.S. PATENT DOCUMENTS 5,800,500 A 9/1998 Spelman et al.
6,801,809 B2 10/2004 Laske et al.
(Continued)

FOREIGN PATENT DOCUMENTS

CN 110237419 9/2019
DE 102018221135 6/2020
(Continued)

*Primary Examiner* — Alyssa M Alter
(74) *Attorney, Agent, or Firm* — Dicke, Billig & Czaja, PLLC (57) ABSTRACT

One aspect relates to a method for producing a ring electrode, including providing an outer element including an outer tube; providing a first inner element, including a first inner tube having a first core made of a sacrificial material, a material of the outer element and a material of the first inner element having a similar microstructure to each other; providing a second inner element, including a second core made of a sacrificial material; forming a composite tube by arranging the first inner element and the second inner element inside the outer element, the first inner element and the second inner element being arranged eccentrically; drawing the composite tube in a longitudinal direction of the composite tube, the material of the outer element and the material of the first inner element retaining a similar microstructure; separating a composite tube disk from the composite tube; removing the sacrificial material of the first core; and removing the sacrificial material of the second core to obtain a contacting opening in the ring electrode.

20 Claims, 4 Drawing Sheets

(56) References Cited

U.S. PATENT DOCUMENTS

| | | |
|---|---|---|
| 7,364,479 B1 | 4/2008 | Deily |
| 8,918,188 B2 | 12/2014 | Tiedtke |
| 10,933,233 B2 * | 3/2021 | Leitold .................. A61N 1/362 |
| 2008/0161887 A1 | 7/2008 | Hagen |
| 2008/0299309 A1 | 12/2008 | Fisk |
| 2013/0237789 A1 | 9/2013 | Cattaneo |
| 2013/0338745 A1 | 12/2013 | Ollivier |
| 2014/0261985 A1 | 9/2014 | Selkee |
| 2016/0303366 A1 | 10/2016 | Childers et al. |
| 2016/0324573 A1 | 11/2016 | Mickelson et al. |
| 2017/0182310 A1 | 6/2017 | Troetzschel et al. |
| 2019/0091473 A1 | 3/2019 | Walter et al. |

FOREIGN PATENT DOCUMENTS

| | | |
|---|---|---|
| EP | 1128869 | 9/2001 |
| EP | 3185248 | 6/2017 |
| EP | 3530314 | 8/2019 |
| WO | 00/27469 | 8/2000 |
| WO | 2008/127478 | 10/2008 |
| WO | 2009/044216 | 4/2009 |

* cited by examiner

RING ELECTRODE WITH INTERMEDIATE DIFFUSION LAYER

CROSS-REFERENCE TO RELATED APPLICATION

This Utility Patent Application claims priority to German Application No. 10 2020 118 372.0 filed on Jul. 13, 2020, which is incorporated herein by reference.

TECHNICAL FIELD

One aspect relates to a method for producing a ring electrode, to a corresponding ring electrode, to an electrode system including such a ring electrode, and to the use of the ring electrode or the electrode system in a cardiac pacemaker and/or for neurostimulation. The ring electrode is generally intended for use as or in an active implantable medical device, but can also be used otherwise. It can be used for signal detection and/or for stimulation.

BACKGROUND

The typically very small component size of a ring electrode for an active implantable medical device and the even smaller dimensions of its sub-features require very expensive and complex production plants and production methods with many individual operations. Conventionally, ring electrodes are produced by machining such as turning from a bar material, and the excess material inside the ring is removed by spark erosion, for example. The ring electrodes are often manufactured from noble metal, such as platinum alloys, and therefore the machining and the removal of the excess material lead to considerable noble metal losses and cost disadvantages. Ring electrodes can also be composed of multiple parts. In this case, there is frequently the problem of permanently and fixedly connecting these parts to each other so that the ring electrode can withstand even continuous and/or frequent stress, for example by the action of force or heat. In the case of multilayer ring electrodes, for example, the individual layers can become detached from each other by mechanical and/or thermal stress, which is also referred to as delamination.

For these and other reasons there is a need for the present embodiment.

SUMMARY

An object of one embodiment is to solve one or more of the aforementioned and other problems of the prior art. For example, one embodiment allows simple and cost-effective production of ring electrodes with multiple openings. Furthermore, one embodiment provides multi-lumen ring electrodes with improved stability, in particular resistance to delamination.

These objects are achieved by the methods and devices described herein, particularly those described in the claims.

Embodiments are described below.

1. A method for producing a ring electrode, comprising the following steps:
   (a) providing an outer element comprising an outer tube,
   (b) providing a first inner element, which comprises a first inner tube having a first core made of a sacrificial material, the first inner tube comprising a diffusion agent on the outer side of the first inner tube, and/or the outer tube comprising a diffusion agent on the inner side of the outer tube,
   (c) providing a second inner element, which comprises a second core made of a sacrificial material,
   (d) forming a composite tube by arranging the first inner element and the second inner element inside the outer element, the first inner element and the second inner element being arranged eccentrically to each other,
   (e) drawing the composite tube in a longitudinal direction of the composite tube,
   (f) forming an integral connection between the outer element and the first inner element by means of the diffusion agent,
   (g) separating a composite tube disk from the composite tube,
   (h) removing the sacrificial material of the first core, and
   (i) removing the sacrificial material of the second core to obtain a contacting opening in the ring electrode.

2. The production method according to embodiment 1, wherein the composite tube is heated to connect the outer element to the first inner element and optionally the second inner element by diffusion bonding by means of the diffusion agent, wherein the composite tube is preferably heated to at least 50%, preferably at least 60% or at least 65% of the melting temperature of the diffusion agent.

3. The production method according to any one of the preceding embodiments, wherein the second inner element comprises a second inner tube which surrounds the second core, wherein the second inner tube further comprises a diffusion agent on the outer side of the second inner tube.

4. The production method according to any one of the preceding embodiments, wherein the diffusion agent is selected from the group consisting of Au, Pd, Ti, Ni, Co, Cr, Fe, Ag, and an active solder.

5. The production method according to embodiment 4, wherein the diffusion agent has a lower melting point than the outer tube, the first inner tube and/or optionally the second inner tube.

6. The production method according to any one of the preceding embodiments, wherein the outer tube, the first inner tube and/or optionally the second inner tube are coated with the diffusion agent by means of electroplating, dip coating, CVD, PVD or by applying a film.

7. The production method according to any one of the preceding embodiments, wherein the diffusion agent is applied to the outer tube, the first inner tube and/or optionally the second inner tube with a layer thickness of 100 nm to 100 µm.

8. The production method according to any one of the preceding embodiments, wherein in step (e) the outer element and the first inner element and optionally the second inner tube are each connected to each other without gaps.

9. The production method according to any one of the preceding embodiments, wherein the outer tube and the first inner tube and optionally the second inner tube comprise a noble metal, a non-noble metal and/or a ceramic material, wherein the non-noble metal is preferably Ti, MP35, 316L, 301 or 304.

10. The production method according to any one of the preceding embodiments, wherein the outer tube and the first inner tube and optionally the second inner tube each substantially consist of the same material, or different materials.

11. The production method according to any one of the preceding embodiments, wherein the sacrificial material of the first core and/or the sacrificial material of the second core comprise a non-noble metal, preferably Cu, Ni or Fe.

12. A ring electrode produced using a method according to any one of the preceding embodiments.

13. A composite tube for producing a ring electrode, comprising an outer element, a first inner element, and a second inner element, wherein the outer element comprises an outer tube, wherein the first inner element comprises a first inner tube with an outer side, wherein the first inner element and the second inner element are arranged inside the outer element, and the first inner element and the second inner element are arranged eccentrically to each other to form a composite tube, wherein a diffusion agent is arranged on the outer side of the first inner tube and/or on the inner side of the outer tube.

14. The composite tube according to embodiment 13, wherein the second inner element comprises a second inner tube which surrounds the second core, wherein the second inner tube further comprises a diffusion agent on the outer side of the second inner tube.

15. A ring electrode, comprising an outer element, a first inner element and a second inner element, wherein the outer element comprises an outer tube, wherein the first inner element comprises a first inner tube with an outer side, wherein the first inner element and the second inner element are arranged inside the outer element, and the first inner element and the second inner element are arranged eccentrically to each other to form a composite tube, wherein the outer element, the first inner element and the second inner element are drawn together in a longitudinal direction of the composite tube, wherein the outer element is connected to the first inner element by an integral connection by means of a diffusion agent.

16. An electrode system comprising a ring electrode according to any one of embodiments 12 or 15 and a conductor element, wherein the conductor element is connected to a contacting opening in the ring electrode.

17. The use of a ring electrode according to any one of embodiments 12 or 15 or of a composite tube according to embodiment 13 or 14 or of an electrode system according to embodiment 16 for producing an implantable medical sensor or stimulator.

BRIEF DESCRIPTION OF THE DRAWINGS

Further features, advantages and possible applications of the present invention can be found in the following description of the exemplary embodiments and in the figures. All features described and/or illustrated form the subject matter of the invention by themselves and in any combination, also independently of their composition in the individual claims or the dependency references thereof. In the figures, like reference signs designate like or similar objects.

DETAILED DESCRIPTION

In the following Detailed Description, reference is made to the accompanying drawings, which form a part hereof, and in which is illustrated by way of illustration specific embodiments in which the embodiment may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiment. The following detailed description, therefore, is not to be taken in a limiting sense, and the scope of the present embodiment is defined by the appended claims.

It is to be understood that the features of the various exemplary embodiments described herein may be combined with each other, unless specifically noted otherwise.

In principle, for the embodiments described herein, the elements of which "have" or "comprise" a particular feature (e.g., material), a further embodiment is always considered in which the element in question consists solely of the feature, i.e. includes no further components. The word "comprise" or "comprising" is used herein in a synonymous manner with the word "have" or "having".

If an element is designated with the singular in one embodiment, an embodiment in which a plurality of these elements are present is also considered. The use of a term for an element in the plural fundamentally also includes an embodiment in which only a single corresponding element is present.

Unless otherwise indicated or clearly excluded from the context, it is possible in principle and is clearly considered herewith that features of different embodiments can also be present in the other embodiments described herein. It is also considered, in principle, that all features described herein in connection with a method are also applicable to the products and devices described herein, and vice versa.

For reasons of brevity only, all of these considered combinations are not explicitly listed in all cases. In principle, technical solutions which are known to be equivalent to the features described herein are also intended to be included in the scope of the embodiment.

A first aspect of one embodiment relates to a method for producing a ring electrode, including the following steps:
(a) providing an outer element including an outer tube,
(b) providing a first inner element, which includes a first inner tube having a first core made of a sacrificial material, the first inner tube including a diffusion agent on the outer side of the first inner tube, and/or the outer tube including a diffusion agent on the inner side of the outer tube,
(c) providing a second inner element, which includes a second core made of a sacrificial material,
(d) forming a composite tube by arranging the first inner element and the second inner element inside the outer element, the first inner element and the second inner element being arranged eccentrically to each other, (e) drawing the composite tube in a longitudinal direction of the composite tube, (f) forming an integral connection between the outer element and the first inner element by using the diffusion agent, (g) separating a composite tube disk from the composite tube, (h) removing the sacrificial material of the first core, and (i) removing the sacrificial material of the second core to obtain a contacting opening in the ring electrode.

In one embodiment, the method includes the following steps:

(a) providing an outer element including an outer tube, (b) providing a first inner element, which includes a first inner tube having a first core made of a sacrificial material, the first inner tube including a diffusion agent on the outer side of the first inner tube, and/or the outer tube including a diffusion agent on the inner side of the outer tube, (c) providing a second inner element, which includes a second core made of a sacrificial material, (d) forming a composite tube by arranging the first inner element and the second inner element inside the outer element, the first inner element and the second inner element being arranged eccentrically to each other, (e) drawing the composite tube in a longitudinal direction of the composite tube, (f) forming an integral connection between the outer element and the first inner element by using the diffusion agent, (g) separating a composite tube disk from the composite tube, (h) removing the sacrificial material of the first core, and (i) removing the sacrificial material of the second core to obtain a contacting opening in the ring electrode.

The steps of the method can be performed in the order indicated above or can be performed in a different order.

At least one component for producing the ring electrode, for example the outer element, the first inner element and/or the second inner element, has a diffusion agent. A diffusion agent is a material which enables or improves the bonding of two components in that the diffusion agent at least partially permeates into the material of at least one of the components, in one embodiment into the material of both components, by diffusion. This process is also referred to as diffusion bonding.

Diffusion bonding is generally understood to mean a process in which two bodies of different materials which are otherwise difficult to connect to each other are brought into a stable connection. Here, under suitable temperature and pressure conditions, two different materials are brought into contact and held under these conditions for a certain time. Under these usually elevated temperatures and pressures compared with normal conditions on the connecting face of the two materials, a mass transfer takes place between the two bodies, which can produce a very stable connection between the two bodies. Such a connection is included herein in the term "integral connection".

The diffusion agent is in one embodiment arranged in such a way that it allows the connection of two components for producing the ring electrode by diffusion bonding. The diffusion agent can be arranged on one or more of the components, for example on the outer side of the first inner tube or on the inner side of the outer tube, or both. In principle, the term "components" refers to all the components of the composite tube, in particular the outer tube, the first inner tube and optionally the second inner tube. The diffusion agent is in one embodiment arranged on the outer side of the first inner tube. Alternatively or additionally, the diffusion agent can be arranged on the outer side of the second inner tube and/or on the inner side of the outer tube.

Multiple components of the composite tube are connected to each other by using the diffusion agent. For example, the diffusion agent forms an integral connection between the outer element and the first inner element. For this purpose, the diffusion agent can be arranged between the outer element and the first inner element, for example on the outer side of the first inner tube or on the inner side of the outer tube, or both. Under the action of elevated pressure and/or elevated temperature, a mass transfer of the diffusion agent into the outer element and/or the first inner element takes place, which is referred to herein as diffusion bonding. The diffusion agent is thereby completely or partially absorbed into the outer element/or the first inner element. If the diffusion agent is completely absorbed by the components of the composite tube, these components can be connected to each other in such a way that the original interface between them is no longer detectable. In this way, a material composite with uniform material properties or a continuous material gradient can be formed. The ring electrodes contained thereby are distinguished by a particular thermal and mechanical load-bearing capacity. In addition, the individual components can be dimensioned smaller in terms of their diameter and/or their wall thickness. Even if portions of the diffusion agent remain between the two components after the diffusion bonding, a better connection between the components can be achieved than would be the case without the diffusion agent. With the aid of the diffusion agent, it is also possible to interconnect components consisting of materials which, without the diffusion agent, cannot enter into a fixed connection with each other by diffusion bonding, for example because they are covered by an oxide layer under normal conditions. As a result, the diffusion agent allows the use of new materials and new material combinations for multilayer ring electrodes. This also makes it possible to use non-metals for individual components, for example the first inner tube. For example, the first inner tube can include titanium.

Suitable diffusion media are in particular metals and alloys. In one embodiment, the diffusion agent is selected from the group consisting of Au, Pd, Ti, Ni, Co, Cr, Fe, Ag, and an active solder. In one embodiment, the diffusion agent is selected from the group consisting of Au, Pd, Ti, Ni, Co, Cr, Fe, Ag, Sn, and an active solder.

Examples of groups of suitable active solders are, for example, silver-titanium solders, silver-copper-titanium solders and silver-copper-indium-titanium solders. In one embodiment, the active solder is AgTi4 or AgCuTi3. Further examples of active solders are 96Au4Ti, 98Au2Ti, 50Ti50Ni, 96.4Au3Ni1Ti, 92.75Cu2Al3Si2.25Ti, 67Ti33Ni, 96Ag4Ti, 70Ti15Cu15Ni, 98.4Ag1In0.6Ti, 60Ti25Ni15Cu, 92.75Ag5Cu1Al1.25Ti, 68.8Ag26.7Cu4.5Ti, 63Ag35.25Cu1.75Ti, 63Ag34.25Cu1.75Ti1Sn, 60.3Ag23Cu14.7In2Ti, 59Ag27.25Cu12.5In1.25Ti, 43.6Ag29.1Cu24.3In3Ti, and 96.4Au3Ni0.6Ti.

In one embodiment, the second material has a melting point of more than 250° C., more than 300° C., 400° C., 500° C., 600° C., 700° C., 800° C., 900° C. or more than 1000° C. In one embodiment, the second material has a hardness of at least 50 HV. In one embodiment, the second material has a tensile strength of at least 200 MPa. In one embodiment, the second material has a modulus of elasticity of at least 100 GPa. In one embodiment, the second material is integrally connected to the outer wall. In one embodiment, the second material is free of lead, tin, bismuth and/or silver. In one embodiment, the second material is free of platinum. In one embodiment, the second material is free of lead, tin, bismuth, platinum and/or silver.

In one embodiment, the diffusion agent is not soldering tin or comparable solder material.

In order to facilitate the formation of an integral connection, the components can be pressed against each other and/or heated.

For this purpose, for example, the composite tube can be heated to at least 50%, in one embodiment at least 60% or at least 65% of the melting temperature of the diffusion agent. For example, the composite tube is heated to 50 to 80%, 60 to 70% or 65 to 70% of the melting temperature of the diffusion agent.

The melting temperature, also referred to as melting point, of a material can either be obtained from the literature or determined with simple experiments. The melting point can be determined using DSC calorimetry. A suitable device for determination is the DSC 204 F1 Phoenix manufactured by Nietzsch, Selb, Germany. The melting temperature described herein refers to the absolute melting temperature measured in Kelvin. For example, if the material of the diffusion agent has a melting point of 1500 K, a temperature of 50% of the melting temperature in this case is 750 K. Thus, the composite tube could in this case be heated to a temperature of at least 750 K in order to connect the outer element and the first inner element to each other by diffusion.

The choice of temperature can be selected, for example, depending on the choice of materials of the components of the composite tube, in particular depending on the materials of the outer tube and the first inner tube. In one embodiment, a temperature corresponding to approximately 50-90% of the higher melting material of the components to be connected is selected. For the materials according to the embodiment, this can be between 100° C. and 3000° C., in one embodiment between 500° C. and 2700° C., in one embodiment between 700° C. and 2500° C. In one embodiment, the temperatures are selected to be below the lowest melting material of a component of the composite tube involved in the connection by using the diffusion material, the temperature in one embodiment being above the melting temperature of the diffusion agent itself. In one embodiment, the composite tube is heated to a temperature below the melting temperature of the sacrificial material. In one embodiment, the composite tube is heated to a temperature below the melting temperature of the sacrificial material but above the melting temperature of the diffusion agent. In one embodiment, the diffusion agent has a lower melting point than the outer tube, the first inner tube and/or optionally the second inner tube. In one embodiment, the diffusion agent has a lower melting point than the outer tube, the first inner tube, and/or optionally the second inner tube, and a lower melting point than the sacrificial material.

Individual or multiple components of the composite tube can be coated with a diffusion agent by various methods. In one embodiment, the first inner tube and/or optionally the second inner tube are coated with the diffusion agent by using electroplating, dip coating, CVD, PVD or by applying a film.

The term PVD or physical vapor deposition refers to a group of vacuum-based coating methods. In contrast to methods of chemical vapor deposition, the starting material is converted into the gas phase with the aid of physical methods. The gaseous material is then guided to the substrate to be coated, where it condenses and forms the target layer.

Examples of PVD methods are thermal evaporation, electron beam evaporation, pulsed laser deposition or pulsed laser ablation, arc evaporation (arc PVD), molecular beam epitaxy, sputtering, ion beam assisted deposition (IBAD), ion plating and ionized cluster beam deposition (ICB).

In CVD, also referred to as chemical vapor deposition, a solid component is deposited out of the gas phase as a layer on the surface of a substrate due to a chemical reaction.

In this case, volatile compounds of the layer components deposit a solid layer, frequently at an elevated temperature of the substrate or component. The CVD method is characterized by at least one chemical reaction on the surface of the substrate or component. At least one gaseous starting compound and at least two reaction products, of which at least one is in the solid phase, must be involved in this reaction.

Particularly preferred are CVD methods which allow deposition at low temperature of the surface to be coated, i.e. of the component or substrate, for example plasma enhanced chemical vapor deposition (plasma enhanced CVD, PECVD) or HFCVD (hot filament CVD) methods.

In one embodiment, the diffusion agent is applied to a component of the composite tube, for example to the outer tube, the first inner tube and/or optionally the second inner tube, with a layer thickness of 100 nm to 100 µm. For example, the diffusion agent is applied with a layer thickness of 100 nm to 500 nm, 100 nm to 1000 nm, 500 nm to 5000 nm, 1 µm to 5 µm, 1 µm to 10 µm, 5 µm to 20 µm or 10 µm to 100 µm.

In one embodiment, a material of the outer element and a material of the first inner element have a similar degree of deformation and/or a similar microstructure and/or hardness to each other. For example, the material of the outer tube and the material of the first inner tube can have a similar microstructure to each other. This means, for example, that in each case the crystal grains of a metal have a similar size and/or shape in both materials.

The degree of deformation or degree of strain can be understood as the logarithmic ratio of the length of a sample after deformation to a length of the sample before deformation.

If an inner component, such as the first inner tube, has an equal or greater Vickers hardness in comparison with an adjacent outer component, e.g. the outer tube, this can improve the stability of the ring electrode produced. In particular, delamination of the outer tube and the first inner tube can be prevented or reduced.

In some embodiments, the ratio C:D is from 0.8 to 1.0; in one embodiment from 0.9 to 1.0; from 0.95 to 1.0, or from 0.99 to 1.0, where C is the hardness of the material of the outer tube, and D is the hardness of the material of the inner tube. The Vickers hardness can be determined by the test methods described hereinafter.

In one embodiment, the composite tube is drawn with a degree of deformation of between 3 and 30% per individual drawing operation and in one embodiment with a degree of deformation of between 3 and 20% per individual drawing operation. In the overall composite after multiple or all drawing operations, the degree of deformation can be between 50 and nearly 100%.

In one embodiment, the outer tube and/or one or all of the inner tubes are soft-annealed prior to drawing to promote flowing of the individual tubes into spaces between the individual tubes.

The outer tube, the first inner tube and/or optionally the second inner tube can each include a metal, for example a noble metal or a non-noble metal. Examples of preferred metals are Pt, Ir, Cu, Ta, Pd, Ti, Au, Mo, Nb, W, Ni, Ti, MP35, 316L, 301, 304, and alloys of these metals and multilayer material systems. In one embodiment, the noble metal is a metal selected from the group consisting of Ru, Rh, Pd, Ag, Os, Ir, Cu, Pt, Au, and Hg.

In some embodiments, the outer tube, the first inner tube, and/or the second inner tube include one or more of the metals Pt, Ir, Cu, Ta, Pd, Ti, Fe, Au, MP35N, or a mixture or alloy thereof. In some embodiments, the outer tube, the first inner tube, and/or the second inner tube include the alloys MP35, PtIr10, PtIr20, 316L, 301 or Nitinol. The outer tube, the first inner tube and/or the second inner tube can also include multilayer material systems. In one embodiment, the outer tube, the first inner tube and/or the second inner tube include MP35, Au, Ta, Pt, Ir, Cu, Pd or Ti. In some embodiments, the outer tube, the first inner tube, and/or the second inner tube contain less than 3%, 2%, or less than 1% Fe.

MP35 is a nickel-cobalt-based temperable alloy. A variant of MP35 is described in industry standard ASTM F562-13. In one embodiment, MP35 is an alloy including 33 to 37% Co, 19 to 21% Cr, 9 to 11% Mo and 33 to 37% Ni.

PtIr10 is an alloy of 88 to 92% platinum and 8 to 12% iridium.

PtIr20 is an alloy of 78 to 82% platinum and 18 to 22% iridium.

316L is an acid-resistant CrNiMo austenite steel with approx. 17% Cr; approx. 12% Ni and at least 2.0% Mo. A variant of 316L is described in industry standard 10088-2. In one embodiment, 316L is an alloy including 16.5 to 18.5% Cr; 2 to 2.5% Mo and 10 to 13% Ni.

301 is a chromium-nickel steel with high corrosion resistance. A variant of 301 is described in industry standard DIN 1.4310. In one embodiment, 301 is an alloy including 16 to 18% Cr and 6 to 8% Ni.

Nitinol is a shape-memory nickel-titanium alloy having an ordered cubic crystal structure and a nickel content of approximately 55%, the remaining portion being titanium. Nitinol has good biocompatibility and corrosion resistance properties. Unless otherwise stated, all percentages indicated herein are to be understood as mass percent (% by weight).

The outer tube, the first inner tube and/or optionally the second inner tube can each independently of each other include or consist of one or more of the aforementioned metals and alloys. In one embodiment, the outer tube, the first inner tube and/or optionally the second inner tube include the same metal or alloy. In one embodiment, the outer tube, the first inner tube and/or optionally the second inner tube each include different materials, for example different metals or alloys. For example, the outer tube and the first inner tube can each include a noble metal; or the outer tube can include a noble metal, while the first inner tube includes a non-noble metal. In one embodiment, the noble metal is a metal selected from the group consisting of Ru, Rh, Pd, Ag, Os, Ir, Cu, Pt, Au, and Hg. In one embodiment, the non-noble metal is a metal other than the metals Ru, Rh, Pd, Ag, Os, Ir, Cu, Pt, Au, and Hg.

If, for example, the outer tube and the inner tube consist of the same material, a particularly firm connection of these two elements can be achieved. However, the diffusion agent allows individual components of the composite tube to be connected to each other comparatively firmly even if they have different materials. In one embodiment, the first inner tube and/or optionally the second inner tube includes titanium. In one embodiment, the first inner tube includes titanium, and the sacrificial material in the first inner tube includes copper. In one embodiment, the second inner tube includes titanium, and the second sacrificial material includes copper. In one embodiment, the outer tube includes platinum, and the first inner tube and/or optionally the second inner tube includes titanium. In one embodiment, the outer tube includes platinum, and the first inner tube and/or optionally the second inner tube includes a non-noble metal.

An advantage of one embodiment resides in the fact that the ring electrode does not have to be produced from the solid material, such as, for example, a rod material, but can be produced directly from hollow tubes. In this way, it is possible to dispense with a cutting or material-removing machining of the outer diameters of the tubes, and significantly less noble metal is used and lost in the interior of the ring electrode, since the tubes do not have a noble metal core which has to be removed. This eliminates not only the costs and the effort for the machining and the material removal, but also the costs of the noble metal and the noble metal losses.

The contacting opening in the ring electrode can be used for electrical and/or mechanical contacting with a conductor element. The contacting opening can thus be used as an electrical connecting element and/or as a mechanical fastening element for the conductor element. The conductor element can be a cable or a wire for contacting the ring electrode with a medical device such as a cardiac pacemaker.

The composite tube can be formed by inserting the first inner element and the second inner element into the outer element. In this case, a defined interface can be produced with, for example, a defined material quality between the outer element, the first inner element and/or the second inner element. For example, a defined material quality of the interface of the contacting opening for the conductor element can be created, so that the contacting of the conductor element on the ring electrode can be particularly secure and reproducible, for example by crimping, clamping or insertion.

The eccentric arrangement of the first inner element and the second inner element relative to each other can be understood such that the center points or centers of gravity of the two inner elements do not lie one on top of the other in cross section. The first inner element and the second inner element are therefore not arranged concentrically and therefore do not form the shape of a target. One inner element can at least partially cover the other inner element, and the two inner elements can lie next to each other, but they have no common center point or center of gravity in cross section. In this way, the contacting opening can be formed such that it lies outside the center point of the ring electrode when viewed in cross section.

Drawing or drawing through can be understood to mean forming under combined tensile and compressive conditions, in which a starting wire is brought to a reduced diameter in multiple steps by using a drawing die or female mold. When the composite tube is drawn, the outer and inner elements can flow toward each other and reduce and possibly even close spaces therebetween. For example, the first inner tube can flow around the second inner element such that the second inner element protrudes nose-like into the first inner tube.

By drawing, it is possible at least in part to achieve a positive fit and/or frictional connection between the individual components of the composite tube, so that a final geometry of the ring electrode is stable after the present production method. This can be understood to mean that the individual components of the composite tube keep together by mutual mechanical blocking and/or friction. Drawing also makes it possible, at least in part, to achieve an integral connection, for example by cold-welding the individual components of the composite tube. This can be understood to mean that the individual components of the composite tube keep together by chemical or atomic connection.

In one embodiment, the outer element and the first inner element are arranged concentrically to each other. This can be understood to mean that the center points or centers of gravity of the outer element and of the first inner element lie one on top of the other in cross section. In this way, a cylindrical main opening of the ring electrode can be formed.

In one embodiment, the diameter of the first inner element is greater than the diameter of the second inner element. In one embodiment, the diameter of the first inner element is more than twice the diameter of the inner element. Further in one embodiment, the diameter of the first inner element is more than three times the diameter of the second inner element. In this way, the main opening of the ring electrode formed by the first inner element is considerably larger than the contacting opening formed by the second inner element.

In one embodiment, the removal of the sacrificial material of the first core includes pickling or etching. In one embodiment, the removal of the sacrificial material of the sacrificial material of the second core includes pickling or etching. The removal of the sacrificial material of the first core and the removal of the sacrificial material of the second core can be performed by the same or a different type of pickling or etching. Pickling can be understood to mean the treatment of the ring electrode or its components by using a pickle. Aggressive chemicals such as acids or alkalis can be used as pickles. Etching can be understood to mean the removal of material of the ring electrode or its components by the use of an etchant. Chemical substances which change (usually oxidize) the material to be etched in a chemical reaction and thus bring it into solution can be used as etchants. Etchants can be acids or strong oxidants. The pickling or etching can be assisted by ultrasound, heat and/or electrical current.

In one embodiment, the sacrificial material of the first core is removed using an acid. In one embodiment, the sacrificial material of the second core is removed using an acid. The same acid can, but does not have to, be used in each case. The acid can be nitric acid, hydrochloric acid, hydrogen peroxide and/or the like.

In one embodiment, the second inner element includes a second inner tube which includes the second core. When the composite tube is drawn, the second inner tube can flow into spaces between the outer tube and the first inner tube. The second inner tube and/or the first inner tube can be soft-annealed to promote this flowing.

In one embodiment, the outer tube includes a noble metal or a noble metal alloy. In one embodiment, the first inner tube includes a noble metal or a noble metal alloy. In one embodiment, the optional second inner tube includes a noble metal or a noble metal alloy. The outer tube, the first inner tube and/or the second inner tube can consist of the same or different materials. Noble metals can be understood to be metals, the redox pairs of which have a positive standard potential in relation to the normal hydrogen electrode. The noble metal can be platinum or the like. In one embodiment, a noble metal is a metal selected from the group consisting of Ru, Rh, Pd, Ag, Os, Ir, Cu, Pt, Au, and Hg. The noble metal alloy can be a platinum-iridium alloy or the like, and in particular a PtIr10 or PtIr20 alloy. In one embodiment, the outer tube includes platinum, and the first inner tube and/or optionally the second inner tube includes titanium. In one embodiment, the outer tube includes platinum, and the first inner tube and/or optionally the second inner tube includes a non-noble metal.

In one embodiment, the sacrificial material of the first core is less noble than the material of the first inner tube. In one embodiment, the sacrificial material of the second core is less noble than the material of the first and/or second inner tube. Base metals or non-noble metals can be understood to mean metals, the redox pairs of which have a negative standard potential in relation to the normal hydrogen electrode.

In one embodiment, the first core of sacrificial material includes a non-noble metal or a non-noble metal alloy. In one embodiment, the second core of sacrificial material includes a non-noble metal or a non-noble metal alloy. A non-noble metal alloy can be understood to mean an alloy of one or more non-noble metals or base metals. The sacrificial material of the first core and the sacrificial material of the second core can consist of or include the same or different materials. The non-noble metal alloy can consist of or include copper, a nickel-cobalt base alloy or the like. For better dimensional stability of the (smaller) opening to be produced, the sacrificial material of the second core can be harder than the sacrificial material of the first core. In one embodiment, the first core consists of copper. In one embodiment, the second core consists of a nickel-cobalt base alloy. The nickel-cobalt base alloy can be MP35N or MP35NLT. In one embodiment, the sacrificial material of the first core is selected from Cu, MP35N, Ni, Co, Ti, 316L, 301, 304, ceramic, or plastic. In one embodiment, the sacrificial material of the second core is selected from Cu, MP35N, Ni, Co, Ti, 316L, 301, 304, ceramic, or plastic.

In one embodiment, the sacrificial material of the first core and/or the sacrificial material of the second core include a non-noble metal, in one embodiment copper. In one embodiment, the sacrificial material of the first core and/or the sacrificial material of the second core include a material selected from the list consisting of Cu, MP35N, Ni, Co, Ti, 316L, 301, 304, ceramic, and plastic.

The outer element, all the inner elements and/or all the sacrificial materials can in principle include different materials independently of each other. The material pairings can be chosen as desired in such a way that the sacrificial material can be removed more easily than the surrounding inner element.

In one embodiment, the outer element includes a material selected from the list consisting of Pt, Ir, Cu, Ta, Pd, Ti, Au, W, Mo, MP35N, 316L, 301, 304, and Nb. In one embodiment, the outer tube includes a material selected from the list consisting of Pt, Ir, Cu, Ta, Pd, Ti, Au, W, Mo, MP35N, 316L, 301, 304, and Nb.

In one embodiment, the outer element includes a non-noble metal, for example, MP35N or a stainless steel alloy. Examples of stainless steel alloys are 316L, 301 and 304. In one embodiment, the outer tube includes a non-noble metal, for example MP35N or a stainless steel alloy.

In one embodiment, the first inner element includes a material selected from the list consisting of Pt, Ir, Cu, Ta, Pd, Ti, Au, W, Mo, MP35N, 316L, 301, 304, and Nb.

In one embodiment, the first inner tube includes a material selected from the list consisting of Pt, Ir, Cu, Ta, Pd, Ti, Au, W, Mo, MP35N, 316L, 301, 304, and Nb.

In one embodiment, the first inner element includes a non-noble metal, for example MP35N or a stainless steel alloy. In one embodiment, the first inner tube includes a non-noble metal, for example MP35N or a stainless steel alloy.

In one embodiment, the second inner element includes a material selected from the list consisting of Pt, Ir, Cu, Ta, Pd, Ti, Au, W, Mo, MP35N, 316L, 301, 304, and Nb.

In one embodiment, the second inner tube includes a material selected from the list consisting of Pt, Ir, Cu, Ta, Pd, Ti, Au, W, Mo, MP35N, 316L, 301, 304, and Nb. In one embodiment, the second inner element includes a non-noble metal, for example MP35N or a stainless steel alloy. In one embodiment, the second inner tube includes a non-noble metal, for example MP35N or a stainless steel alloy.

The outer tube and the first inner tube and optionally the second inner tube can each consist substantially of the same material or different materials. In one embodiment, the first inner tube and the second inner tube include a material each independently selected from the list consisting of Pt, Ir, Cu, Ta, Pd, Ti, Au, W, Mo, MP35N, 316L, 301, 304, and Nb.

In one embodiment, the first inner tube and the second inner tube consist of a material each independently selected from the list consisting of Pt, Ir, Cu, Ta, Pd, Ti, Au, W, Mo, MP35N, 316L, 301, 304, and Nb. In one embodiment, the first inner tube and the second inner tube consist of the same material, each independently selected from the list consisting of Pt, Ir, Cu, Ta, Pd, Ti, Au, W, Mo, MP35N, 316L, 301, 304, and Nb. In one embodiment, the first inner tube and the second inner tube consist of Pt or a Pt-containing alloy, for example PtIr10 or PtIr20.

In one embodiment, the outer element includes a noble metal, and the first inner element and/or the second inner element includes a non-noble metal. In one embodiment, the outer tube includes platinum, and the first inner tube and/or optionally the second inner tube includes titanium. In one embodiment, the outer tube includes platinum, and the first inner tube and/or optionally the second inner tube includes a non-noble metal.

In one embodiment, the production method includes cutting the composite tube into rings after the sacrificial materials have been removed. The cutting can be effected contactlessly, for example by wire erosion. For cutting, the composite tube can be fixed with a clamping device and fastened, for example, to a strip.

In one embodiment, the production method includes, after removal of the sacrificial materials and either before or after cutting the composite tube into rings, further processing, which reduces the length of the second inner element in relation to the outer element and/or the first inner element, as seen in a longitudinal section through the ring electrode, so that the second inner element does not extend along the entire length of the outer element and/or the first inner element in longitudinal section. In other words, the second inner element or the contacting opening forms at least one step in the ring electrode. This can be done by mechanical machining and/or an eroding process.

After the removal of the sacrificial materials, a heat treatment and in particular recrystallization annealing can be provided, for example in order to increase the ductility of the ring electrode.

The outer element and all the inner elements can have any desired shapes in cross section and in particular can be circular, oval, elliptical, semicircular, but also square, rectangular, polygonal and the like. The outer element and all the inner elements can have cross sections that differ from one another. In one embodiment, the outer element and all the inner elements are circular in cross section.

In one embodiment, the outer tube and/or one or all of the inner tubes are a profiled tube. A profiled tube can be understood to mean a tube which has a non-circular shape in cross section, such as, for example, a square, rectangular, semicircular or arcuate shape in cross section. In one embodiment, the first inner tube is a profiled tube. The inner tube can in this case be mostly circular in shape, but can have, at least in one location, an arcuate bulge which is designed to receive the second inner element. The profiled tube can also have an arcuate bulge for a further inner element at a further location. The bulge of the profiled tube can also be trapezoidal.

Any numbers and arrangements of openings in a ring electrode can be produced by the production method according to embodiments. By removing the sacrificial material of the first core, a through-opening can be produced in the ring electrode. By removing the sacrificial material of the second core, a contacting opening for electrical and/or mechanical contacting can be produced. By removing a sacrificial material of an optional third core, a further opening can be produced in the ring electrode. In one embodiment, the production method further includes the following steps for this:

providing a third inner element, which includes a third core made of a sacrificial material,
  forming the composite tube by arranging the third inner element inside the outer element, the first, second, and third inner elements being arranged eccentrically to each other; and
  removing the sacrificial material of the third core.

A diffusion agent can be arranged on the outer side of the third inner element. The third inner element can have a third inner tube, which includes the third core of sacrificial material. The sacrificial material of the third core can be removed by pickling or etching as described above. The further opening of the ring electrode created by the removal of the third core can be arranged opposite the contacting opening created by removing the second core on the outer circumference of the first inner tube. The through-opening of the ring electrode created by the removal of the first core can be apple-shaped, so that the contacting opening and the further opening can each be arranged in the opposite bulges of the apple-shaped through-opening on the outer circumference of the contacting opening.

The material of the third inner tube can have a similar microstructure as the material of the outer tube, the material of the first inner tube, and/or the material of the second inner tube.

Correspondingly, further inner elements, each including a further inner tube and a further core of sacrificial material, can be used to produce further contacting openings.

In one embodiment, the obtained composite tube is heated after step (e) to connect the outer element and the first inner element and optionally the second inner tube to each other by using diffusion.

In one embodiment, the composite tube is heated to a temperature of at least 50%, in one embodiment at least 60% or 65% of the melting temperature of the diffusion agent after step (e) to connect the outer element and the first inner element and optionally the second inner tube to each other by using diffusion.

In one embodiment, the heating forms an integral connection of the outer element to the first inner element and optionally the second inner tube.

In one embodiment, the outer element and the first inner element, and optionally the second inner tube, are connected by the heating such that a material composite having a substantially uniform microstructure is formed.

In one embodiment, the method further includes drawing the composite tube again in a longitudinal direction of the composite tube after the heating of the composite tube described above. As a result of the repeated drawing, smaller sized ring electrodes can be produced after the connection of the outer element to the inner element, as described herein.

In one embodiment, the outer tube, the first inner tube, and optionally the second inner tube include a noble metal.

It is further proposed to provide a ring electrode including an outer element, a first inner element, and a second inner element. The outer element includes an outer tube. The first inner element and the second inner element are arranged inside the outer element. The first inner element and the second inner element are arranged eccentrically to each other to form a composite tube. The outer element, the first inner element, and the second inner element have been drawn together in a longitudinal direction of the composite tube. The first inner element has a first inner tube surrounding a first cavity from which a sacrificial material has been removed. The second inner element surrounds a second cavity from which a sacrificial material has been removed and which forms a contacting opening in the ring electrode. At least two selected from the outer element, the first inner element and the second element are connected integrally to each other by using a diffusion agent.

A further aspect of one embodiment relates to a composite tube for producing a ring electrode, including an outer element, a first inner element, and a second inner element, wherein the outer element includes an outer tube, wherein the first inner element includes a first inner tube with an outer side, wherein the first inner element and the second inner element are arranged inside the outer element, and the first inner element and the second inner element are arranged eccentrically to each other to form a composite tube, wherein a diffusion agent is arranged on the outer side of the first inner tube. Alternatively or additionally, the diffusion agent can be arranged on another component of the composite tube, for example on the inner side of the outer tube and/or optionally on the outer side of the second inner tube.

A further aspect of one embodiment relates to a ring electrode, including an outer element, a first inner element and a second inner element, wherein the outer element includes an outer tube, wherein the first inner element includes a first inner tube with an outer side, wherein the first inner element and the second inner element are arranged inside the outer element, and the first inner element and the second inner element are arranged eccentrically to each other to form a composite tube, wherein the outer element, the first inner element and the second inner element are drawn together in a longitudinal direction of the composite tube, wherein the outer element is connected to the first inner element by an integral connection by using a diffusion agent.

Furthermore, a ring electrode is described which is formed from multiple metal layers, wherein at least two of the metal layers are connected integrally to each other by using a diffusion agent. Such metal layers can be, for example, the components of the outer element described herein, as well as of the first and second inner elements. The ring electrode can include an inner through-opening for receiving a multi-wire cable and an internal contacting opening for connection to a single conductor. The connection of the at least two metal layers can be carried out or formed by diffusion bonding. The metal layers can include, for example, platinum or titanium. In one embodiment, one of the metal layers includes platinum and one of the other metal layers includes titanium.

In an embodiment of the above-described variants of a ring electrode, a material of the outer element and a material of the first inner element have a similar microstructure to each other.

For example, the material of the outer tube and the material of the first inner tube can have a similar microstructure to each other. This means, for example, that in each case the crystal grains of a metal have a similar size and/or shape in both materials.

In one embodiment, the ratio A:B is from 0.8 to 1.2; in one embodiment from 0.9 to 1.1; from 0.95 to 1.05, or from 0.99 to 1.01, where A is the average crystal grain size of the outer tube, and B is the average crystal grain size of the first inner tube. The grain size can be determined with the test methods described hereinafter.

In some embodiments, the ratio C:D is from 0.8 to 1.2; in one embodiment from 0.9 to 1.1; from 0.95 to 1.05, or from 0.99 to 1.01, where C is the hardness of the material of the outer tube, and D is the hardness of the material of the inner tube. The Vickers hardness can be determined by the test methods described hereinafter.

In one embodiment, the ring electrode has a boundary line, interface, or "seam" between the outer element and the first inner element when viewed in cross section. This can be understood to mean that the outer element and the first inner element do not completely merge into each other and melt with each other, but the two elements can still be recognized under the microscope as originally different components. In particular, the boundary line can include residual portions of the diffusion agent if the diffusion agent has not completely migrated into the outer element and/or the first inner element. For example, the ring electrode can include between the outer element and the first inner element a substantially continuous layer of the diffusion agent, or can include a region including an increased proportion of the diffusion agent.

Some possible dimensions of the ring electrode are mentioned below. The individual dimensions are to be understood independently of each other and do not necessarily form a common embodiment, but this is possible. An outer diameter of the ring electrode and thus an outer diameter of the outer element and the outer tube can be between 1 and 3 mm, in one embodiment between 1.3 and 2.5 mm and in one embodiment between 1.5 and 2.0 mm. An inner diameter of the first inner element and thus an inner diameter of the first inner tube can be between 0.9 and 2.9 mm, in one embodiment between 1.2 and 2.4 mm and in one embodiment between 1.4 and 1.9 mm. An inner diameter of the contacting opening and thus an outer diameter of the second core can be between 0.10 and 0.30 mm, in one embodiment between 0.15 and 0.25 mm and in one embodiment between 0.17 and 0.20 mm.

In one embodiment, the outer diameter of the outer tube is 0.3 to 3.0 mm, in one embodiment 0.5 to 2 mm. In one embodiment, the inner diameter of the second inner tube is 0.02 to 0.3 mm, in one embodiment 0.04 to 0.2 mm. In one embodiment, the length of the ring electrode is 0.05 to 5 mm, in one embodiment 0.1 to 3 mm. In one embodiment, the wall thickness of the ring electrode is 0.005 to 0.2 mm, in one embodiment 0.01 to 0.1 mm.

It is further proposed to provide an electrode system including such a ring electrode and a conductor element. The conductor element is connected to a contacting opening in the ring electrode. The conductor element can be a wire, a cable or the like. The contacting opening in the ring electrode can be a type of small, inner hole for electrical and/or mechanical contacting of the conductor element. The contacting opening can therefore be a fastening element for the conductor element. The conductor element can be connected to the contacting opening or the fastening element of the ring electrode by welding, in particular laser welding or resistance welding, soldering, crimping or the like. In this way, particularly secure and simple fastening of the conductor element to the ring electrode is achieved. In one embodiment, the conductor element is connected frictionally and integrally to the contacting opening, for example by welding and crimping.

It is furthermore proposed to use such a ring electrode or such an electrode system produced according to the production method described here in a stimulator, for example cardiac pacemaker or for neurostimulation. One embodiment can be used as a stimulation electrode or measuring electrode for cardiac pacemaker electrodes, in particular for ventricular, atrial and left ventricular supply lines. One embodiment can also be used for neurostimulation, for example in spinal cord stimulation, gastric stimulation, peripheral nerve stimulation or deep brain stimulation. Furthermore, use on catheters is possible, for example in electrophysiology applications, such as for ablation, cardiac flow measurement or the like. Of course, other possible uses are also possible. Examples of catheters according to one embodiment are those which are designed for electrophysiological mapping or ablation of tissue. In one embodiment, the ring electrode is designed and/or intended to be connected to a generator of an active implantable device. A ring electrode of one embodiment can also be used in a sensor, i.e. a medical device for picking up an electrical signal. The ring electrodes described herein can also be used in a stimulator. A stimulator is a medical device which can achieve a physiological effect by emitting an electrical signal to the body of a living being. For example, a neurostimulator can effect an electrical signal in a nerve cell (e.g., an action potential) by emitting an electrical signal to the nerve cell.

A further aspect of one embodiment relates to a microelectrode or microelectrode array including a ring electrode described herein.

The ring electrodes described herein do not necessarily have to have a circular cross section. The cross section of the ring electrodes can be oval or elliptical, for example. The outer face and the inner face of the ring electrode in the region of the large through-opening do not necessarily have to be parallel. For example, the cross section of the outer face can be circular, and the cross section of the inner face can be elliptical. An angular shape of the cross section is also possible in principle.

The same applies to the used outer elements, inner elements and the components thereof.

Testing Method

In the absence of specifically mentioned measurement conditions, all measurements are carried out under standard conditions, i.e. at a temperature of 298.15 K and an absolute pressure of 100 kPa.

Hardness

Hardness is the mechanical resistance which a material offers to the mechanical penetration by another body. Hardness can be measured by microindentation. In this case, a diamond test body according to Vickers is pressed into the layer, and the force-displacement curve is recorded during the measurement. The mechanical characteristics, including hardness, of the specimen can then be calculated from this curve. Hardness can be determined, for example, with the device Anton Paar MHT-10 Microhardness Tester. It should be noted that the impression depth should be no more than 10% of the layer thickness, otherwise properties of the substrate can distort the measurements. The Vickers hardness can be determined according to the standard DIN EN ISO 6507-4:2018.

Grain Size

To measure the crystal grain size, a first cross section of the sample to be examined is prepared using metallographic methods. The grain size of the 1st cross section is then measured using a light microscope (Leica DM4000). The light microscope is used to generate a two-dimensional first image of the grain structure of the sample. The grain size of 100 grains is measured. If the first image includes less than 100 grains, another image is generated by creating a further cross section of the sample. The average grain size is calculated from the arithmetic mean of the 100 grain sizes. The grain size is defined as the maximum linear distance which can be measured between 2 points on the grain boundary. For example, if the grain has an elongate shape, the grain size should be measured in the longest direction.

Furthermore, the grain boundary can have a certain width. The width of the grain boundaries is not included in the determination of the grain size.

EXAMPLES

The embodiment is further illustrated below with reference to examples, which, however, should not be understood as limiting. It will be apparent to the person skilled in the art that other equivalent means can be used similarly in place of the features described herein.

The figures illustrate, by way of example, various intermediate and end products of the method according to the embodiment and ring electrodes 10 according to one embodiment. The ring electrode 10 can be used as an active implantable medical device, for example in a cardiac pacemaker or for neurostimulation. It can be used for signal detection and for stimulation.

The method for producing the ring electrode 10 here includes the following steps (not necessarily in this order):

In a step S1, providing an outer element 11 including an outer tube 12, a first inner element 13 including a first inner tube 14 having a first core 15 made of a sacrificial material, and a second inner element 16 including a second core 17 made of a sacrificial material, In a step S2, coating the first inner tube 14 and the second inner tube 15 with a diffusion agent, In a step S3, forming a composite tube by arranging the first inner element 13 and the second inner element 16 inside the outer element 11, the first inner element 13 and the second inner element 16 being arranged eccentrically to each other.

In a step S4, drawing the composite tube in a longitudinal direction of the composite tube, In a step S5, forming an integral connection between the outer tube and the first inner tube and the second inner tube by using the diffusion agent by heating the composite tube to a temperature above the absolute melting temperature of the diffusion agent, In a step S6, separating a composite tube disk from the composite tube, In a step S7, removing the sacrificial material of the first core 15 to obtain a ring electrode 10.

In a step S8, removing the sacrificial material of the second core 17 to obtain a contacting opening 2 in the ring electrode 10.

The provision of the second inner tube 15 is an optional method step, which can be omitted in some embodiments. Instead, the second core 17 can also be provided without the second inner tube 15 surrounding it.

FIGS. 1a to 1e illustrate views of several embodiments of a precursor of the ring electrode 10 after the composite tube is formed, but before the composite tube is drawn. The precursor of the ring electrode 10 includes an outer element 11, a first inner element 13 and a second inner element 16.

Figure 1A:
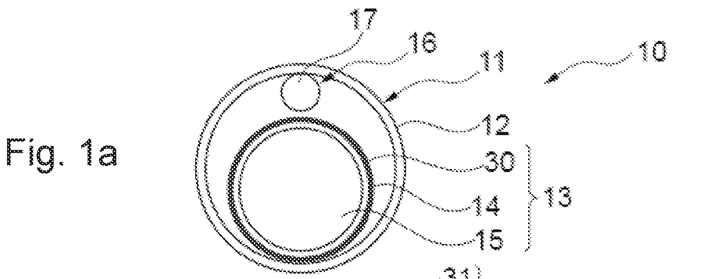
FIGS. 1a-1f illustrate several embodiments of a step of the method for producing a ring electrode.

In particular in the embodiment illustrated in FIG. 1a, the outer element 11 is circular and includes a circular outer tube 12. The first inner element 13 and the second inner element 16 are also circular and lie inside the outer element 11 and its outer tube 12. The first inner element 13 and the second inner element 16 are arranged eccentrically to each other, that is to say the center points of the two inner elements do not lie on top of each other. The diameter of the first inner element 13 is significantly larger than the diameter of the second inner element 16.

The first inner element 13 has a circular first inner tube 14, which surrounds a likewise circular first cavity including a first sacrificial material. The second inner element 16 surrounds a circular second cavity including a second sacrificial material. A diffusion agent 30 is arranged on the outer side of the first inner tube 14.

Here, the outer tube 12 and the first inner tube 13 consist of the alloy PtIr10. Here, the first inner tube 13 is electroplated with a 10 µm thick nickel layer (melting point: 1728 K), which is used as diffusion agent 30. Here, the first core 15 consists of nickel. The second core 17 consists here of 316L. In step S5, an integral connection is produced between the first inner tube 13 and the outer tube 12 by diffusion bonding by heating the composite tube to 1123 K. In the subsequent production step S7, a through-opening 3 can be produced in the ring electrode 10 by removing the sacrificial material of the first core 15. Step S7 can be pickling with hydrochloric acid in an ultrasonic bath at 80° C. In the subsequent production step S8, a contacting opening 2 for electrical and/or mechanical contacting can be produced by removing the sacrificial material of the second core 17. Step S8 can be pickling with FeCl3 in the in an ultrasonic bath for 15 minutes at 60° C. The contacting opening 2 can be used as an electrical connecting element and/or as a mechanical fastening element for a conductor element in order to form an electrode system from the ring electrode 10 and the conductor element.

Figure 1B:
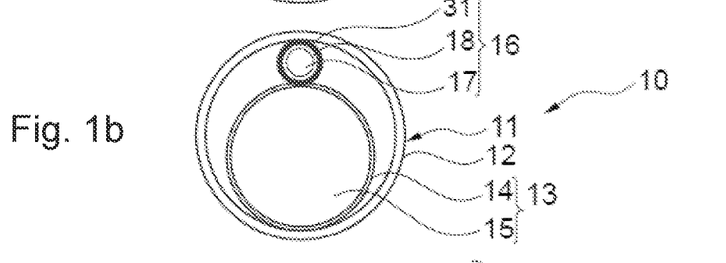

In the embodiment illustrated in FIG. 1b, the second inner element 16 includes a second inner tube 18 including the second core 17. When the composite tube is drawn, the second inner tube 18 can flow into spaces between the outer tube 12 and the first inner tube 13. The second inner tube 18 here likewise consists of PtIr10. A diffusion agent 31 consisting of nickel is arranged on the outer side of the second inner tube 18. In this embodiment, the first inner tube does not include any diffusion agent.

Figure 1C:
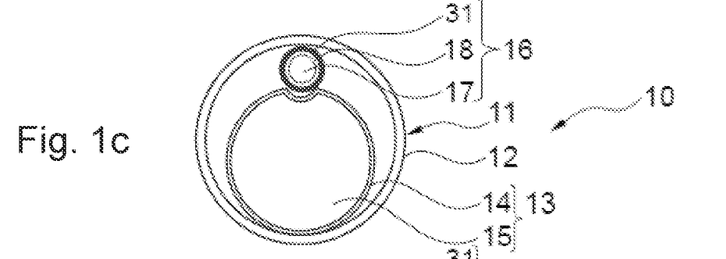
Figures 1D, 1E, 1F:
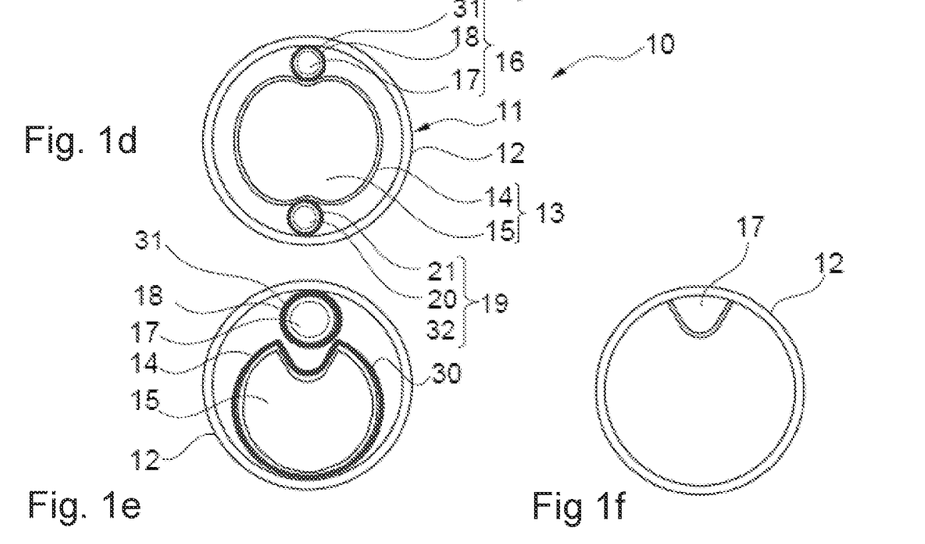

In the embodiments illustrated in FIGS. 1c to 1e, the first inner tube 13 is a profiled tube. The inner tube 13 is mostly circular but in the embodiments illustrated in FIGS. 2c and 2e has an arcuate (FIG. 2c) or trapezoidal (FIG. 2e) bulge in one location in order to accommodate the second inner element 16.

In the embodiment according to FIG. 1c, a diffusion agent 31 is arranged on the outer side of the second inner tube 18. In this embodiment, the first inner tube 14 does not include any diffusion agent.

In the embodiment illustrated in FIG. 1d, the profiled tube of the first inner tube 13 has an arcuate bulge for a further, third inner element 19 at a further location opposite the second inner element 16. The third inner element 19 lies inside the outer element 11, and the first, second and third inner elements are arranged eccentrically to each other. The third inner element 19 includes a third inner tube 21 and a third core 20 made of a sacrificial material, the removal of which results in the production of a further opening in the ring electrode 10. In the embodiment illustrated in FIG. 2d, the removal of the first core 15 creates an apple-shaped through-opening 3 of the ring electrode 10, in which the contacting opening 2 and the further opening are each arranged in the opposite bulges of the apple-shaped through-opening 3. A diffusion agent 31 is arranged on the outer side of the second inner tube 18. A diffusion agent 32 is arranged on the outer side of the third inner tube 21. In this embodiment, the first inner tube 14 does not include any diffusion agent.

In the embodiment illustrated in FIG. 1e, a diffusion agent 30 is arranged on the outer side of the first inner tube 14, and a diffusion agent 31 is arranged on the outer side of the second inner tube 18.

In FIG. 1f, a top view of a precursor of the ring electrode 10 after step S5 illustrated the formation of an integral connection between the outer tube and the first inner tube and the second inner tube by using the diffusion agent. The outer element and the inner elements are fused to form a one-piece material composite.

Figure 2A:
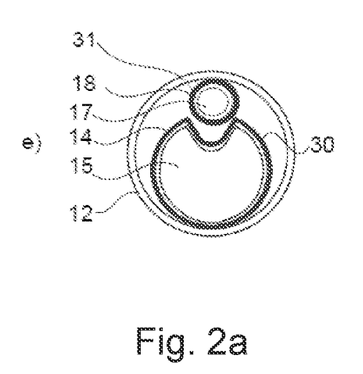
FIGS. 2a-2b each illustrate top views of several embodiments of a precursor of a ring electrode.
Figure 3A:
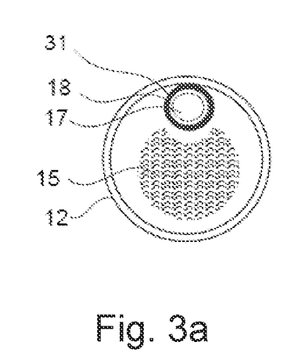
FIGS. 3a-3b each illustrate top views of several embodiments of a precursor of a ring electrode.
Figure 4A:
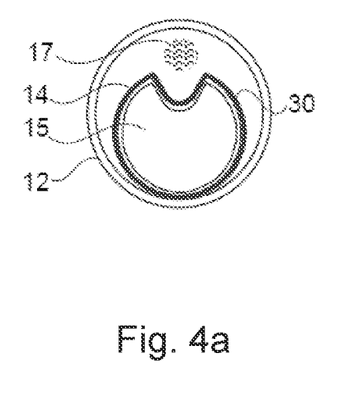
FIGS. 4a-4b each illustrate top views of several embodiments of a precursor of a ring electrode.

FIGS. 2a, 3a and 4a each illustrate top views of several embodiments of a precursor of the ring electrode 10 after step S3, i.e. after the formation of the composite tube, but before step S4, the drawing of the composite tube. The precursor of the ring electrode 10 includes an outer element 11, a first inner element 13 and a second inner element 16.

Figure 2B:
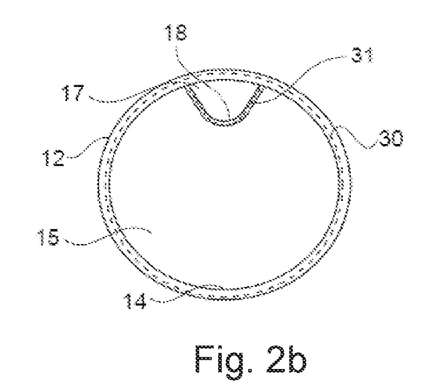
Figure 3B:
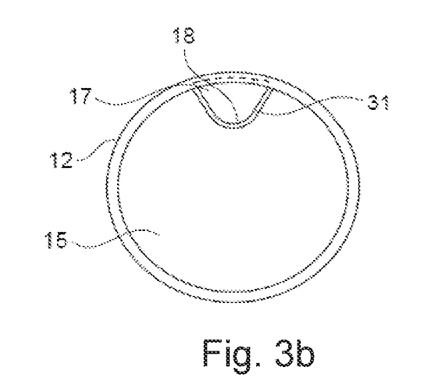
Figure 4B:
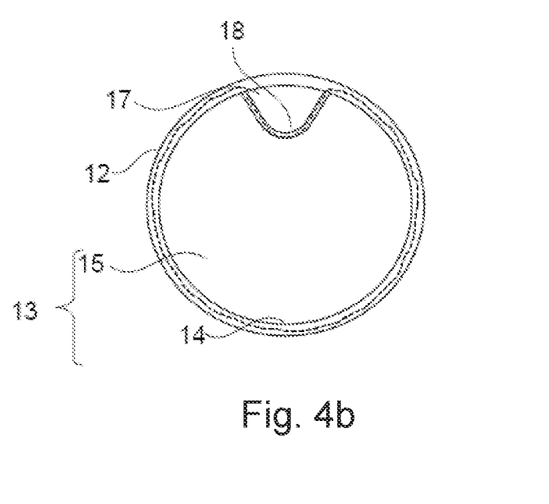

FIGS. 2b, 3b and 4b each illustrate top views of several embodiments of a precursor of the ring electrode 10 after step S5, the formation of an integral connection between the outer tube and the first inner tube and optionally the second inner tube by using the diffusion agent. The outer element and the inner elements are each fused to form a one-piece material composite.

The embodiment of a precursor of a ring element illustrated in FIG. 2a has two elements with diffusion media. The first inner tube 14 includes a diffusion agent 30 on the outer side of the first inner tube 14. The second inner tube 18 includes a diffusion agent 31 on the outer side of the second inner tube 18. By using the diffusion agent 30, 31, the outer tube 12, the first inner tube 14 and the second inner tube 18 can each form an integral connection to each other, so that a one-piece ring electrode with a contacting opening can be produced from the precursor illustrated here.

FIG. 2b illustrates the precursor of the ring electrode from FIG. 2a after the step of forming an integral connection. Along the dashed line, an integral connection is formed between the outer tube 12, the first inner tube 14 and the second inner tube 18 by using the diffusion agent 30, 31. In this embodiment, the integral connection is formed by using the diffusion agent along the entire circumference of the ring electrode and along the entire circumference of the first inner element 13.

By using the diffusion agent both on the first inner tube 14 and on the second inner tube 18, a particularly high composite strength is achieved along the complete surface of the individual elements, so that a particularly stable ring electrode can be produced.

In the embodiment illustrated in FIG. 3a, the precursor of a ring electrode has a second inner tube 18 with a second core 17 and a diffusion agent 31 on the outer side of the second inner tube 18. The second inner tube 18 is used to produce a contacting opening in the ring electrode. The first core 15 is not directly surrounded by a first inner tube or a diffusion layer, but is brought into direct contact with the outer tube 12. This embodiment allows smaller wall thicknesses of the through-opening and/or of the contacting opening of the ring electrode, so that a higher degree of miniaturization and material savings can be achieved.

FIG. 3b illustrates the precursor of the ring electrode from FIG. 3a after the step of forming an integral connection. Along the dashed line, an integral connection is formed between the second inner tube 18 and the outer tube 12 by using the diffusion agent 31.

In the embodiment illustrated in FIG. 4a, the precursor of a ring electrode has a first inner tube 14 with a first core 15 and a diffusion agent 30 on the outer side of the first inner tube 14. The first inner tube 14 is used to produce a through-opening in the ring electrode. The second core 17 is not directly surrounded by a second inner tube or a diffusion layer, but is brought into direct contact with the outer tube 12.

FIG. 4b illustrates the precursor of the ring electrode from FIG. 4a after the step of forming an integral connection. Along the dashed line, an integral connection is formed between the first inner tube 14 and the outer tube 12 by using the diffusion agent 30. In this embodiment, the integral connection is formed by using the diffusion agent along the entire circumference of the first inner tube 14, which corresponds to virtually the entire circumference of the outer tube 12, except for the region of the second core 17, the removal of which later forms a contacting opening.

Figure 5A:
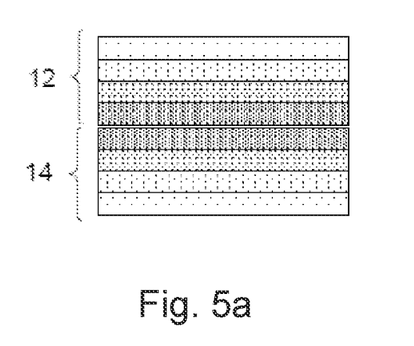
FIGS. 5a-5b illustrate various embodiments of the formation of an integral connection by using a diffusion agent.
Figure 5B:
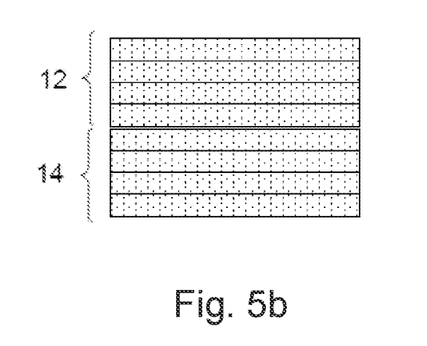

FIG. 5 illustrates, by way of example, two embodiments of the formation of an integral connection between the outer tube 12 and the first inner tube 14 by using a diffusion agent. The diffusion agent is represented by dots. In FIG. 5a there is an increased concentration of the diffusion agent in the plane which forms the contact interface between the outer tube 12 and the first inner tube 14 before the integral connection is formed. In FIG. 5b, the diffusion agent has distributed substantially uniformly within the respective material of the outer tube 12 and the first inner tube 14. In this case, a particularly stable connection can be produced between the outer tube 12 and the first inner tube 14.

Figure 6A:
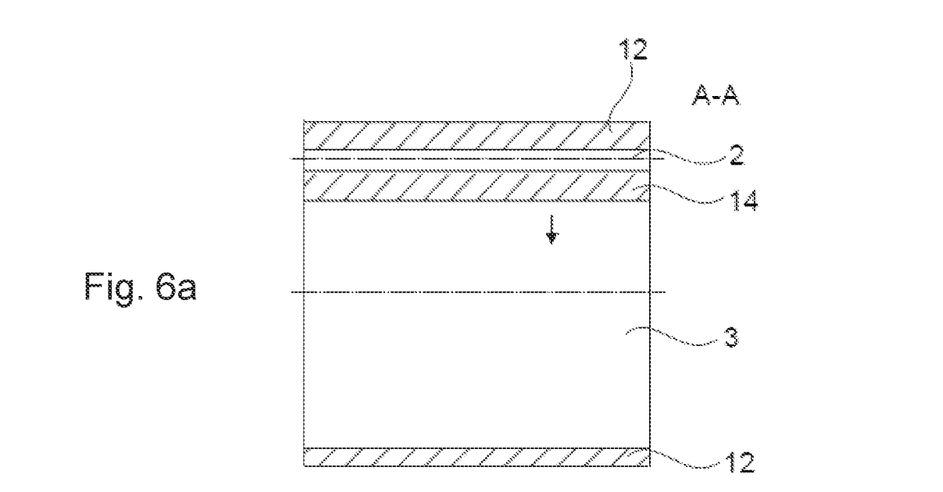
FIGS. 6a-6b illustrate exemplary longitudinal sections through a ring electrode.
Figure 6B:
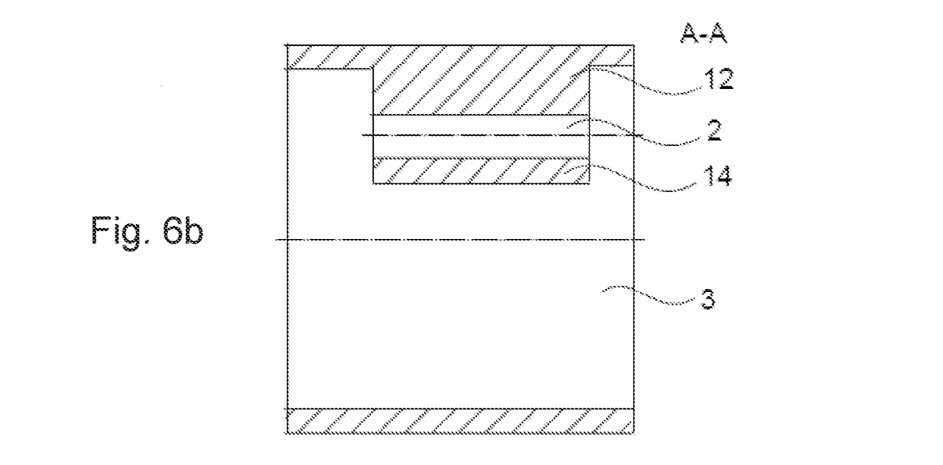

FIGS. 6a and 6b illustrate exemplary longitudinal sections through a longitudinal direction of the ring electrode 10 according to FIG. 3. FIG. 6a illustrates a ring electrode 10 having a constant inner diameter. FIG. 6b illustrates a ring electrode 10 having an asymmetric and stepped inner diameter. The second inner element 16 is reduced in length in comparison with the outer element 11, so that the second inner element 16 and thus the contacting opening 2 do not extend along the entire length of the outer element 11 in longitudinal section. In the ring electrode 10 illustrated in FIG. 6b, the contacting opening 2 ends at its two ends within the outer element 11 of the ring electrode 10, therefore the contacting opening 2 does not terminate flush with the ring electrode 10 at any end.

In addition, it should be noted that "comprising" or "having" does not exclude other elements or steps, and "a" or "an" does not exclude a plurality. Furthermore, it should be noted that features or steps which have been described with reference to one of the above exemplary embodiments can also be used in combination with other features or steps of other exemplary embodiments described above. Reference signs in the claims should not be interpreted as limitations.

Although specific embodiments have been illustrated and described herein, it will be appreciated by those of ordinary skill in the art that a variety of alternate and/or equivalent implementations may be substituted for the specific embodiments illustrated and described without departing from the scope of the present embodiment. This application is intended to cover any adaptations or variations of the specific embodiments discussed herein. Therefore, it is intended that this embodiment be limited only by the claims and the equivalents thereof.

The invention claimed is:

1. A method for producing a ring electrode, comprising:
    (a) providing an outer element comprising an outer tube,
    (b) providing a first inner element, which comprises a first inner tube having a first core made of a sacrificial material,
    the first inner tube comprising a diffusion agent on the outer side of the first inner tube, or the outer tube comprising a diffusion agent on the inner side of the outer tube,
    (c) providing a second inner element, which comprises a second core made of a sacrificial material,
    (d) forming a composite tube by arranging the first inner element and the second inner element inside the outer element, the first inner element and the second inner element being arranged eccentrically to each other,
    (e) drawing the composite tube in a longitudinal direction of the composite tube,
    (f) forming an integral connection between the outer element and the first inner element by means of the diffusion agent,
    (g) separating a composite tube disk from the composite tube,
    (h) removing the sacrificial material of the first core, and
    (i) removing the sacrificial material of the second core to obtain a contacting opening in the ring electrode.

2. The production method according to claim 1, wherein the composite tube is heated to connect the outer element to the first inner element and optionally the second inner element by diffusion bonding by means of the diffusion agent, wherein the composite tube is heated to at least 50% of the melting temperature of the diffusion agent.

3. The production method according to claim 1, wherein the composite tube is heated to connect the outer element to the first inner element and the second inner element by diffusion bonding by means of the diffusion agent, wherein the composite tube is heated to at least 65% of the melting temperature of the diffusion agent.

4. The production method according to claim 1, wherein the second inner element comprises a second inner tube which surrounds the second core, wherein the second inner tube further comprises a diffusion agent on the outer side of the second inner tube.

5. The production method according to claim 1, wherein the diffusion agent is selected from the group consisting of Au, Pd, Ti, Ni, Co, Cr, Fe, Ag, and an active solder.

6. The production method according to claim 5, wherein the diffusion agent has a lower melting point than the outer tube, the first inner tube or the second inner tube.

7. The production method according to claim 1, wherein the outer tube, the first inner tube or the second inner tube are coated with the diffusion agent by means of electroplating, dip coating, CVD, PVD or by applying a film.

8. The production method according to claim 1, wherein the diffusion agent is applied to the outer tube, the first inner tube or the second inner tube with a layer thickness of 100 nm to 100 μm.

9. The production method according to claim 1, wherein in (e) the outer element and the first inner element and the second inner tube are each connected to each other without gaps.

10. The production method according to claim 1, wherein the outer tube and the first inner tube and the second inner tube comprise a noble metal, a non-noble metal and/or a ceramic material, wherein the non-noble metal is Ti, MP35, 316L, 301 or 304.

11. The production method according to claim 1, wherein the outer tube and the first inner tube and the second inner tube each substantially consist of the same material, or different materials.

12. The production method according to claim 1, wherein the sacrificial material of the first core and/or the sacrificial material of the second core comprise a non-noble metal, Cu, Ni or Fe.

13. A ring electrode produced by a method according to claim 1.

14. An electrode system comprising a ring electrode according to claim 13 and a conductor element, wherein the conductor element is connected to a contacting opening in the ring electrode.

15. The use of an electrode system according to claim 14 for producing an implantable medical sensor or stimulator.

16. The use of a ring electrode according to claim 13 for producing an implantable medical sensor or stimulator.

17. A composite tube for producing a ring electrode, comprising:
an outer element;
a first inner element; and
a second inner element;
wherein the outer element comprises an outer tube;
wherein the first inner element comprises a first inner tube with an outer side;
wherein the first inner element and the second inner element are arranged inside the outer element, and the first inner element and the second inner element are arranged eccentrically to each other to form a composite tube; and
wherein a diffusion agent is arranged on the outer side of the first inner tube or on the inner side of the outer tube.

18. The composite tube according to claim 17, wherein the second inner element comprises a second inner tube which surrounds the second core, wherein the second inner tube further comprises a diffusion agent on the outer side of the second inner tube.

19. The use of a composite tube according to claim 17 for producing an implantable medical sensor or stimulator.

20. A ring electrode, comprising:
an outer element;
a first inner element; and
a second inner element;
wherein the outer element comprises an outer tube;
wherein the first inner element comprises a first inner tube with an outer side;
wherein the first inner element and the second inner element are arranged inside the outer element, and the first inner element and the second inner element are arranged eccentrically to each other to form a composite tube;
wherein the outer element, the first inner element and the second inner element are drawn together in a longitudinal direction of the composite tube; and
wherein the outer element is connected to the first inner element by an integral connection by means of a diffusion agent.

* * * * *